(12) United States Patent
Christensen (10) Patent No.: US 8,092,436 B2
(45) Date of Patent: Jan. 10, 2012

(54) BODILY FLUID DRAINAGE ASSEMBLY

(75) Inventor: Earl G. Christensen, Provo, UT (US)

(73) Assignee: Sterigear LLC, Provo, UT (US)

( * ) Notice: Subject to any disclaimer, the term of this patent is extended or adjusted under 35 U.S.C. 154(b) by 565 days.

(21) Appl. No.: 12/253,714

(22) Filed: Oct. 17, 2008

(65) Prior Publication Data

US 2010/0100062 A1  Apr. 22, 2010

(51) Int. Cl.
*A61M 1/00* (2006.01)
(52) U.S. Cl. .......... 604/318; 73/232; 73/290 R; 206/534
(58) Field of Classification Search .............. 604/246, 604/318, 322, 327, 540; 206/534; 73/54.15, 73/61.43, 232, 290 R
See application file for complete search history.

(56) References Cited

U.S. PATENT DOCUMENTS

| | | |
|---|---|---|
| 4,153,163 A | 5/1979 | Alderman et al. |
| 4,173,979 A | 11/1979 | Odis |
| 4,606,736 A | 8/1986 | Van De Weghe |
| 4,874,387 A | 10/1989 | Boone |
| 5,056,685 A | 10/1991 | Wild |
| 5,211,642 A | 5/1993 | Clendenning |
| 5,226,564 A | 7/1993 | Steer et al. |
| 5,489,281 A | 2/1996 | Watanabe et al. |
| 5,496,299 A | 3/1996 | Felix et al. |
| D391,483 S | 3/1998 | Freeman |
| 5,725,515 A | 3/1998 | Propp |
| 6,053,905 A | 4/2000 | Daignault, Jr. et al. |
| 6,096,007 A | 8/2000 | Haan et al. |
| 6,132,407 A | 10/2000 | Genese et al. |
| D438,616 S | 3/2001 | Williams |
| 6,482,190 B1 | 11/2002 | Genese et al. |
| 6,613,036 B1 | 9/2003 | Farmer et al. |
| 6,955,272 B2 | 10/2005 | Collins |
| D515,699 S | 2/2006 | Girod |
| 7,001,370 B2 | 2/2006 | Kubalak et al. |
| 7,500,968 B1 | 3/2009 | Nappa et al. |
| 7,513,894 B2 | 4/2009 | Howlett |
| 2003/0060786 A1 | 3/2003 | Olsen et al. |
| 2004/0240520 A1 | 12/2004 | Faries et al. |
| 2005/0059952 A1 | 3/2005 | Giuliano et al. |
| 2006/0111681 A1 | 5/2006 | Vernon |
| 2007/0203463 A1 | 8/2007 | Salvadori et al. |
| 2007/0282296 A1 | 12/2007 | Matsuda et al. |
| 2009/0024099 A1 | 1/2009 | Burgess et al. |
| 2009/0030386 A1 | 1/2009 | Kim et al. |
| 2009/0088709 A1 | 4/2009 | Salvadori |

OTHER PUBLICATIONS

Drainage Bag Cover; Western Home Medical; www.westernhomemedical.com.
Privacy cover for Urinary Drainage Bags; Access to Recreation. www.store.accesstr.com.
Urine Drain Bag Holder; http://cgi.ebay.ca.

*Primary Examiner* — Melanie Hand
(74) *Attorney, Agent, or Firm* — Stoel Rives LLP (57) ABSTRACT

A bodily fluid drainage assembly having one or more covers and a fluid bag. The fluid bag has a first and a second volume indicator. The first volume indicator is employed by comparing a top level of a fluid with graduations that make up the first volume indicator. The second volume indicator and one of the covers can be used to appreciate an approximate volume of the fluid without directly observing the fluid. Any covers present on the assembly can be removed.

27 Claims, 9 Drawing Sheets

BODILY FLUID DRAINAGE ASSEMBLY

TECHNICAL FIELD

The present disclosure relates generally to the field of medical devices. More specifically, the present disclosure relates to a bodily fluid drainage assembly.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the disclosure's scope, the embodiments will be described and explained with specificity and detail in reference to the accompanying drawings.

| Index of Elements Identified in the Drawings | |
|---|---|
| 100 | bodily fluid drainage assembly |
| 110 | fluid bag |
| 111 | outer edge |
| 112 | front panel |
| 113 | seam |
| 114 | outlet tube holder |
| 115 | upper portion |
| 116 | lower portion |
| 117 | first volume indicator |
| 121 | inlet tube |
| 122 | outlet tube |
| 123 | outlet regulator |
| 124 | hanger |
| 130 | first cover |
| 131 | outer edge |
| 132 | inner edge |
| 133 | seam |
| 134 | perforations |
| 135 | second volume indicator |
| 136 | fluid level indicator |
| 137 | graduations |
| 138 | cutout |
| 140 | second cover |
| 141 | outer edge |
| 142 | inner edge |
| 143 | seam |
| 144 | perforations |
| 148 | cutout |
| 150 | fluid |
| 200 | bodily fluid drainage assembly |
| 210 | fluid bag |
| 211 | outer edge |
| 212 | front face |
| 213 | seam |
| 215 | upper portion |
| 216 | lower portion |
| 217 | first volume indicator |
| 221 | inlet tube |
| 222 | outlet tube |
| 224 | hanger |
| 230 | first cover |
| 231 | outer edge |
| 232 | inner edge |
| 233 | seam |
| 234 | perforations |
| 235 | second volume indicator |
| 236 | fluid level indicator |
| 237 | graduations |
| 240 | second cover |
| 241 | outer edge |
| 242 | inner edge |
| 243 | seam |
| 244 | perforations |
| 250 | fluid |
| 260 | third cover |
| 261 | window cover |
| 262 | window |
| 263 | cutout |
| 264 | perforations |
| 265 | outer edges |
| 300 | bodily fluid drainage assembly |
| 310 | fluid bag |
| 311 | outer edge |
| 312 | front face |
| 317 | first volume indicator |
| 318 | left portion |
| 319 | right portion |
| 321 | inlet tube |
| 322 | outlet tube |
| 324 | hanger |
| 330 | cover |
| 331 | outer edge |
| 332 | inner edge |
| 333 | seam |
| 334 | perforations |
| 335 | second volume indicator |
| 336 | fluid level indicator |
| 337 | graduations |
| 350 | fluid |
| 400 | bodily fluid drainage assembly |
| 410 | fluid bag |

-continued

Index of Elements Identified in the Drawings

| | |
|---|---|
| 430 | first cover |
| 440 | second cover |
| 500 | bodily fluid drainage assembly |
| 510 | fluid bag |
| 530 | first cover |
| 540 | second cover |
| 600 | bodily fluid drainage assembly |
| 610 | fluid bag |
| 630 | first cover |
| 640 | second cover |
| 700 | bodily fluid drainage assembly |
| 710 | fluid bag |
| 730 | first cover |
| 740 | second cover |

DETAILED DESCRIPTION OF PREFERRED EMBODIMENTS

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the disclosure, as claimed, but is merely representative of various embodiments. While the various aspects of the embodiments are presented in drawings, the drawings are not necessarily drawn to scale unless specifically indicated.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other. The term "abutting" refers to items that are in direct physical contact with each other, although the items may not necessarily be attached together.

Figure 1:
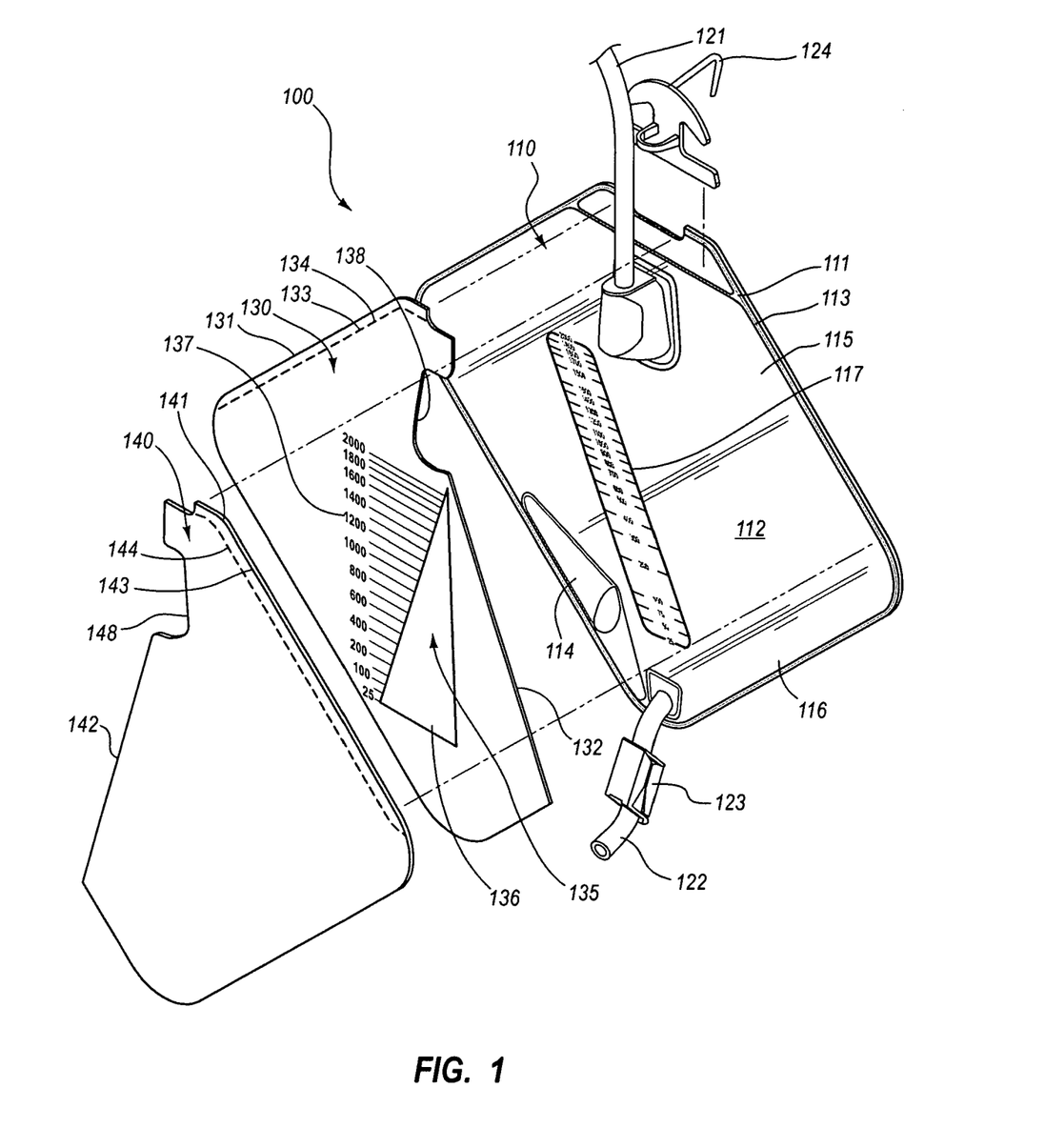
FIG. 1 is an exploded perspective view of a bodily fluid drainage assembly.
Figure 2:
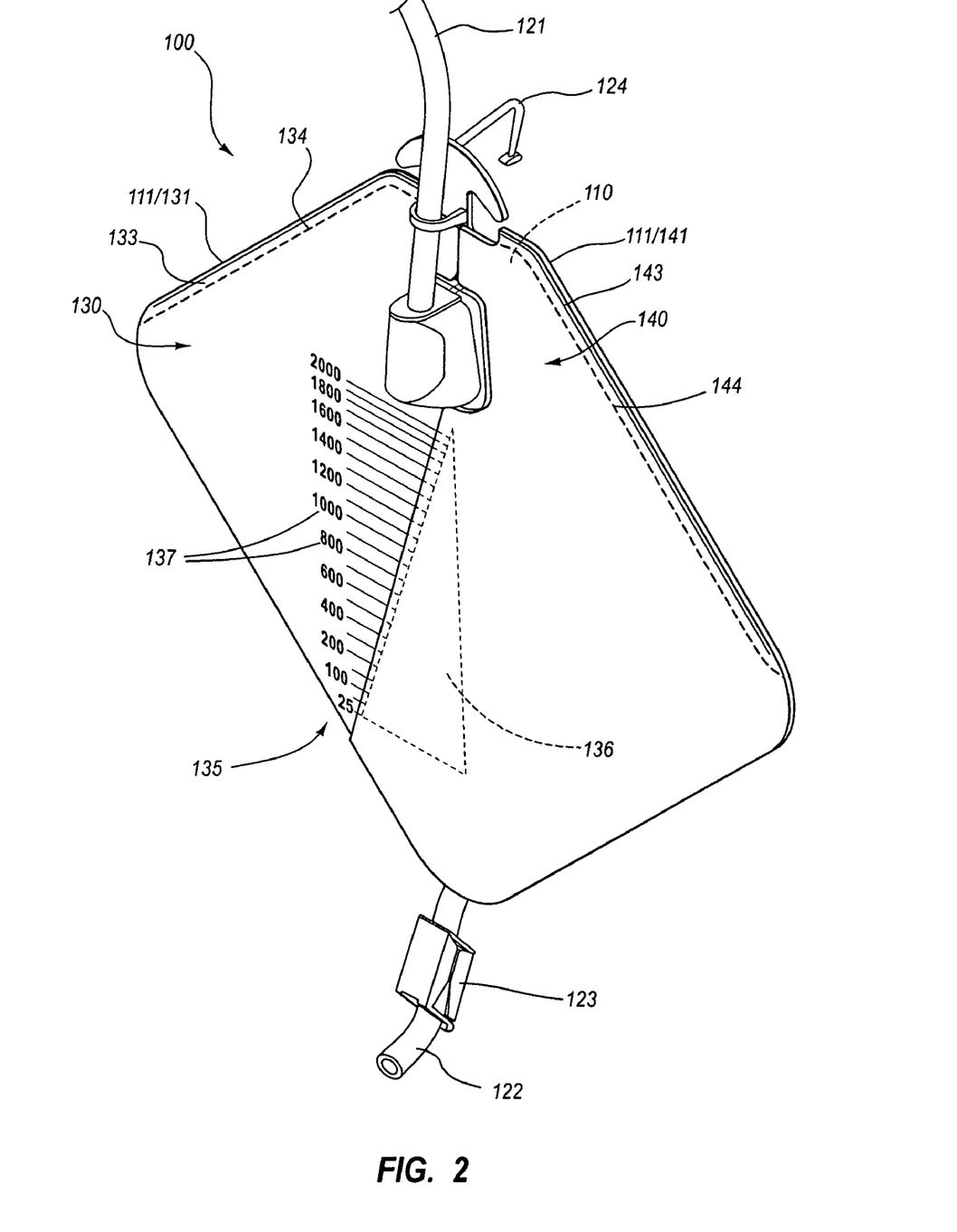
FIG. 2 is a perspective view of the bodily fluid drainage assembly of FIG. 1 after the assembly has been assembled.

FIGS. 1-2 depict drainage bodily fluid drainage assembly 100, from a front elevation view, wherein FIG. 1 is an exploded-perspective view and FIG. 2 is a perspective view after the assembly has been assembled. Bodily fluid drainage assembly 100 may comprise a fluid bag 110, a first cover 130 and a second cover 140. Assembly 100 is configured to receive bodily fluid; optionally retain the fluid; at least partially obscure the visibility of the fluid while allowing an approximate volume of the fluid to be determined; and optionally allow the fluid to be directly viewed by at least partially removing a portion of the assembly. Drainage bag 110 and first and second covers 120 and 130 may comprise polyvinyl chloride, polyurethane, vinyl or any other suitable material known in the art.

Drainage bag 110 may comprise one or more panels of a liquid impervious material, wherein at least a portion of the front panel 112 is substantially transparent or semitransparent such that a liquid contained within the bag may be readily observed. The panels may be joined along an outer edge 111 via radio frequency (RF) welding, heat sealing, gluing, or any other suitable technique. Once joined, the two panels comprise a seam 113 adjacent to outer edge 111. When coupled together, the panels form a fillable void that may receive fluid via an inlet tube 121 and a corresponding inlet aperture (not visible) that are located on upper portion 115 of bag 110. Approximate volume of fluid within the bag may be ascertained via a first volume indicator 117, which may comprise graduations marked on front panel 112 of bag 110. In the depicted embodiment, graduations 117 denote various predetermined volumes and may be printed on the fluid bag. In another embodiment, the graduations may comprise raised or recessed portions of the fluid bag that are formed during or after manufacturing of the fluid bag. The graduations may represent any predetermined measurement of volume, such as fluid ounces and/or Milliliters and may vary in their distribution accordingly. Additionally, the space between graduations may not be uniform within the scale to account for a non-linear rate of rise in fluid level to account for expansion of the fluid bag. In the depicted embodiment, graduations 117 are located on a right hand portion (as seen from the viewer's perspective) of fluid bag 110; however, in other embodiments, the graduations may be located anywhere on fluid bag 110. Since at least a portion of front panel 112 is translucent, the top of the fluid can be compared to the graduations and an approximate volume of the fluid can be determined.

As will be determined by those skilled in the art, a variety of types and configurations of fluid bags can be utilized without departing from the scope and spirit of the present disclosure. For example, the fluid bag may be manufactured using a one-piece method, wherein the bag comprises a single piece of plastic that is folded along one or more edges. Further, the shape and size of assembly 100 is for illustrative purposes only and may vary.

A hanger 124 is located in a non-fillable portion of upper portion 115 and is configured to allow assembly 100 to be suspended from a patient, or a nearby structure such as a wheelchair, bed, or stand. Hanger 124 may comprise a hook-like extension, an aperture, or both. The hanger may comprise one or more pieces of plastic and may be coupled to assembly 100 via RF welding, heat sealing, gluing, hardware, or any other suitable technique. In another embodiment, hanger 124 may be coupled to assembly 100 such that it may be removed. In another embodiment, hanger 124 may comprise an aperture in bag 110 and/or first and second covers 130 and 140.

An outlet tube 122 and corresponding drainage bag outlet aperture (not visible) are located on a bottom portion 116 of the fluid bag. The outlet tube 122 may allow a fluid contained within bag 110 to be drained from the bag or retained within the bag via an output regulator 123. Output regulator 123 may comprise a plastic or metal clip, in-line valve, or any other suitable structure. Fluid bag 110 may further comprise an outlet tube holder 114 that comprises a slot, loop, or hook that is configured to receive and reversibly retain outlet tube 122 in an at least partially upright position.

As will be determined by those skilled in the art, a variety of types and configurations of bodily fluid drainage bags can be utilized without departing from the scope and spirit of the present disclosure. For example, the size, shape, and proportions of the fluid bag may vary (See FIGS. 6-9). Additionally, the size, shape, and proportions of the inlet and outlet tubes, as well as the materials from which the fluid bag and tubes are manufactured may vary. For example, in one embodiment, the hanger comprises a contiguous extension of the bag and in another embodiment, the hanger comprises an aperture in the bag.

Bodily fluid drainage assembly 100 may further comprise first cover 130 that is an opaque material and which may comprise a similar shape as fluid drainage bag 110. First cover 130 has an outer edge 131 that may be at least partially aligned with outer edge 111 of fluid bag 110. When first cover 130 is coupled to bag 110, a seam 133 may be formed along outer edge 111. The first cover may be coupled to the fluid drainage bag via RF welding, heat sealing, gluing, hardware, or any other suitable technique. Cover 130 may be coupled to bag 110 only along outer edge 131, or in another embodiment, the cover is coupled to the bag along more than one edge.

Cover 130 further comprises perforations 134 that are located adjacent to seam 133 and are configured to allow cover 130 to be at least partially removed from bag 110.

Cover 130 further comprises an interior edge 132 that may have a cutout 138 that partially surrounds the junction of inlet tube 121 and fluid bag 110. A second volume indicator 135 is located on first cover 130 and comprises a fluid level indicator 136 and graduations 137. The function of second volume indicator 135 is described in text associated with FIGS. 3A-3B, below.

Second cover 140 may comprise an opaque material that may be identical to first cover 130. The second cover may comprise an outer edge 141, an inner edge 142, a seam 143, perforations 144, and a cutout 148. As with first cover 130, second cover 140 may be coupled to bag 110 along outer edge 141 to form seam 143. Perforations 144 may be formed in cover 140 along that seam such that the cover may be at least partially removed. First and second covers 130 and 140 may be coupled to fluid bag 110 during manufacture of the bag such that seams and 133 and/or 143 are formed at the same time.

As will be determined by those skilled in the art, a variety of types and configurations of first and second covers may be used without deviating from the spirit of the present disclosure. For example, the first and second covers may or may not be coupled to the lower portion of the fluid bag and the covers may not extend all the way to the bottom of the fluid bag. First and second covers may be configured to be removable without employing perforations; for example, the seams may be configured to rupture when tension is applied for them or reversible fasteners may be used such as snaps, clips, zippers, hooks and loops closures, or removable glue.

Figure 3A:
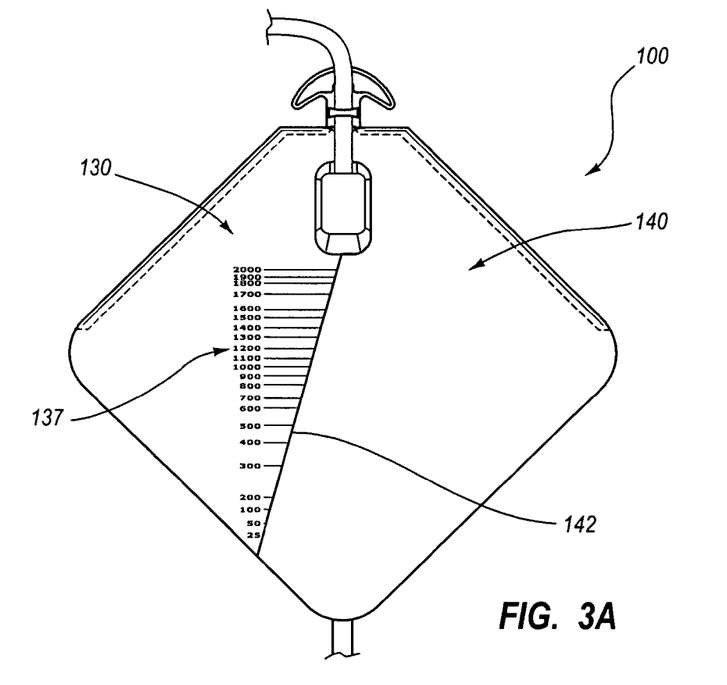
FIG. 3A is a front elevation view of the bodily fluid drainage assembly of FIG. 1, after the bodily fluid drainage assembly has received some fluid.
Figure 3B:
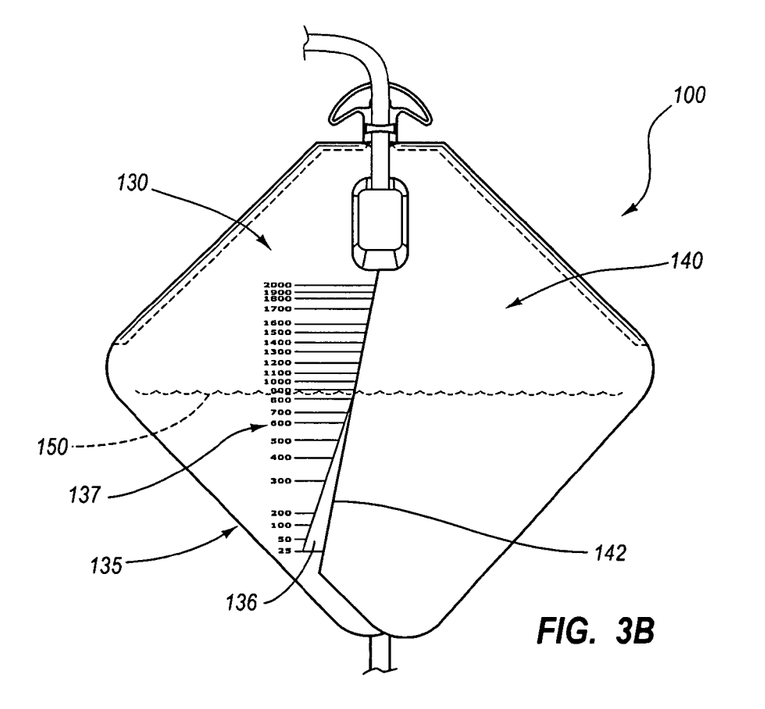
FIG. 3B is a front elevation view of the bodily fluid drainage assembly of FIG. 3A after the bodily fluid drainage assembly has received some fluid.
Figure 3C:
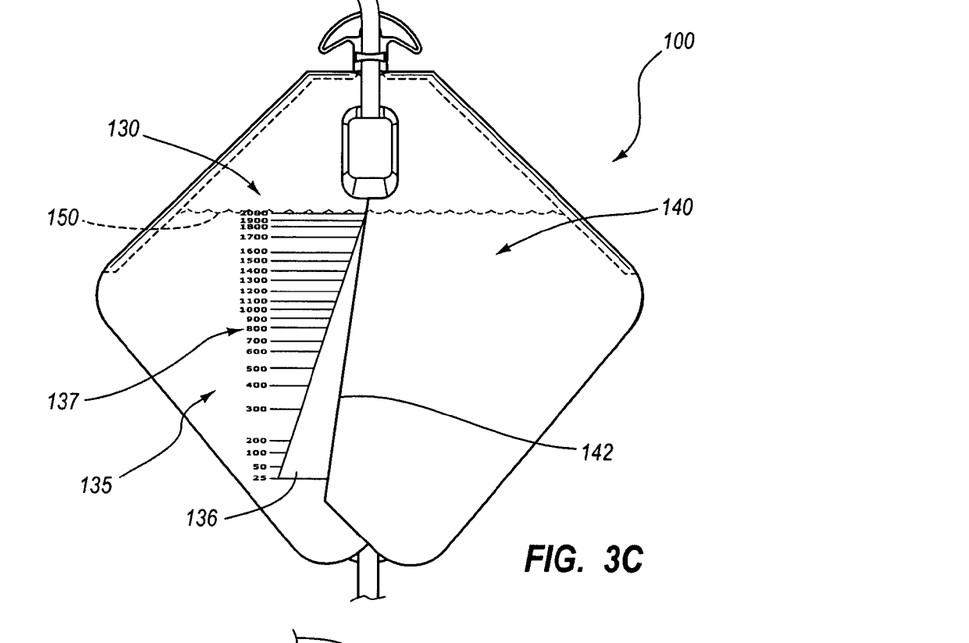
FIG. 3C is a front elevation view of the bodily fluid drainage assembly of FIG. 3A after the bodily fluid drainage assembly has received additional fluid.
Figure 3D:
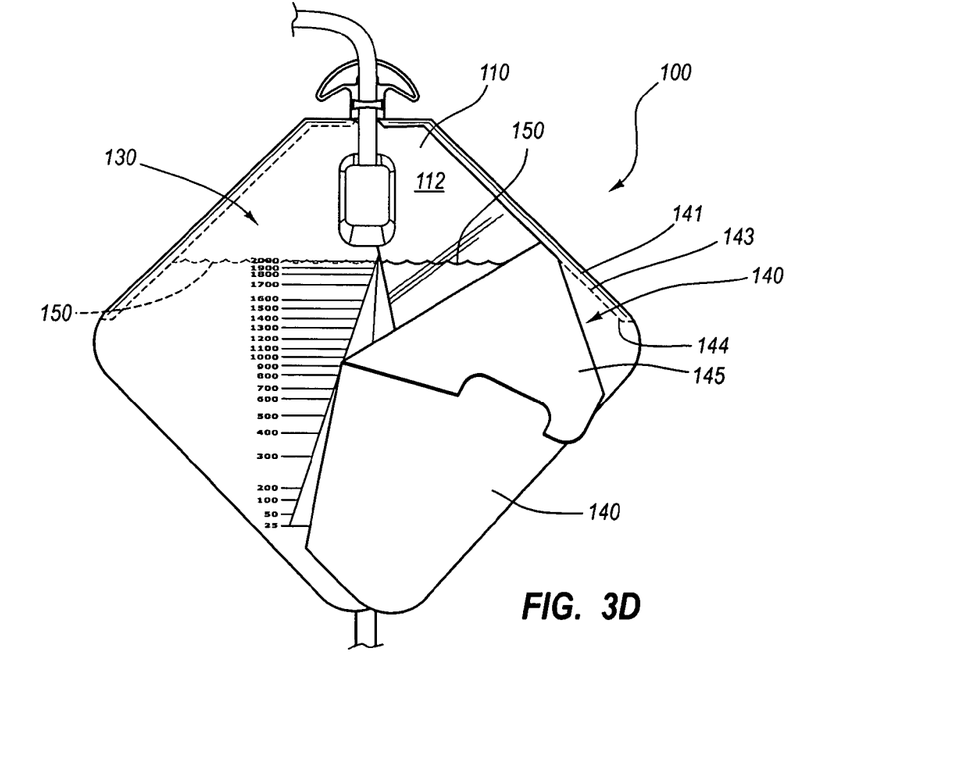
FIG. 3D is a front elevation view of the bodily fluid drainage assembly of FIG. 3A after a portion of the bodily fluid drainage assembly has been torn.

FIGS. 3A-3D depict bodily fluid drainage assembly 100 from a front elevation view, wherein in FIG. 3A, the assembly does not contain fluid; in FIG. 3B, the assembly has received some fluid; in FIG. 3C the assembly has received some more fluid; and in FIG. 3D, the second cover of the assembly has been partially torn away. In the depiction of FIG. 3A bodily fluid drainage assembly is in an empty, planar configuration. Opaque first and second covers 130 and 140 obscure the fluid bag. Graduations 137 of the second volume indicator are visible, but partially obscured by inner edge 142 of second cover 140.

When assembly 100 receives fluid 150, as depicted in FIG. 3B, the assembly changes configurations from substantially planar to a more rounded or ovalized configuration. As a result, first cover 130 and second cover 140 slide over each other such that the position of inner edge 142 on second volume indicator 135 is altered. In the depiction of FIG. 3B, the assembly has received enough fluid that inner edge 142 has slid far enough that fluid level indicator 136 has become visible. The approximate volume of the liquid may be determined by identifying among graduations 137 those that are adjacent to the uppermost portion of the fluid level indicator 136 that is visible before inner edge 142 obscures the fluid level indicator. As such, an approximate volume of a fluid within bodily fluid drainage assembly 100 may be ascertained without directly viewing the fluid within the fluid bag.

In the depiction of FIG. 3C, assembly 100 has received additional fluid 150 such that inner edge 142 of second cover 140 has slid further over first cover 130 and second volume indicator 135. Inner edge 142 has revealed more of fluid level indicator 136, such that a new approximate volume is indicated by the fluid level indicator, graduations 137 and inside edge 142 of second cover 140. As shown in FIG. 3C, inner edge 142 has slid across fluid level indicator 136 to reveal the indicator up to the approximate level of fluid 150.

FIG. 3D depicts assembly 100 as shown in FIG. 3D after a portion of second cover 140 has been removed. If a person would like to directly observe fluid 150 through front panel 112 of bag 110, second cover 140 may be partially or completely removed from assembly 100 via rupturing perforations 144. In the depiction of FIG. 3D, a portion of second cover 140 has been torn from assembly 100 to form a flap 145. Likewise, first cover 130 may be partially or completely removed such that the graduations (not shown) located on front panel 112 may be used to estimate the volume of the fluid contained within bag 100. Fluid 150 may be temporarily visualized without removing first cover 130 and/or second cover 140 by lifting a bottom portion of the cover(s).

FIGS. 4A-4D depict another embodiment of a bodily fluid drainage assembly 200. Assembly 200 may be configured similarly and may function similarly as assembly 100, described herein. Drainage assembly 200 may comprise a fluid bag 210, a first cover 230, a second cover 240, and a third cover 260. Fluid bag 210 may comprise an outer edge 211, a front face 212, a seam 213, an upper portion 215, a lower portion 216, a first volume indicator 217, an inlet tube 221, an outlet tube 222, and a hanger 224.

Figure 4A:
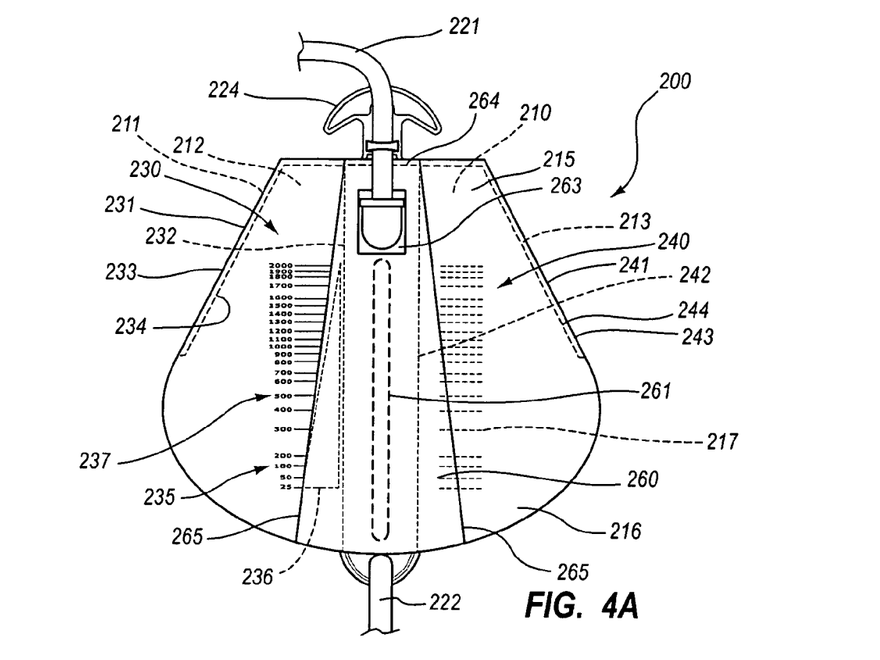
FIG. 4A is a front elevation view of another embodiment of a bodily fluid drainage assembly.

Fluid bag 210 may comprise one or more pieces a plastic material that are coupled together to form a bag that can retain fluid that has an outer edge 211 that defines a perimeter of the bag. Adjacent to the outer edge is a seam 213 that may be formed by coupling the one or more plastic pieces together via RF welding or any other suitable technique. In the depicted embodiment, an inlet tube 221 and hanger 224 are located on an upper portion 215 and an outlet tube 222 is located on a lower portion 216 of fluid bag 210. At least a portion of fluid bag 210 may be at least partially translucent; for example, at least a portion of front face 212 may be translucent, such that various characteristics of a fluid contained within the fluid bag may be determined. First volume indicator 217 may be printed, stamped, or otherwise marked on fluid bag 210. In the depicted embodiment, first volume indicator 217 comprises graduations that demark approximate volumes of a fluid contained within the fluid bag.

First cover 230 may comprise a partially opaque material that is coupled to fluid bag 210. First cover 230 may comprise an outer edge 231, an inner edge 232, a seam 233, perforations 234, and a second volume indicator 235. Second volume indicator may comprise a fluid level indicator 236 and graduations 237. Second cover 240 may comprise an outer edge 241, an inner edge 242, a seam 243 and perforations 244. Third cover 260 may comprise a window cover 261, a window 262, a cutout 263, perforations 264, and outer edges 265.

Figure 4B:
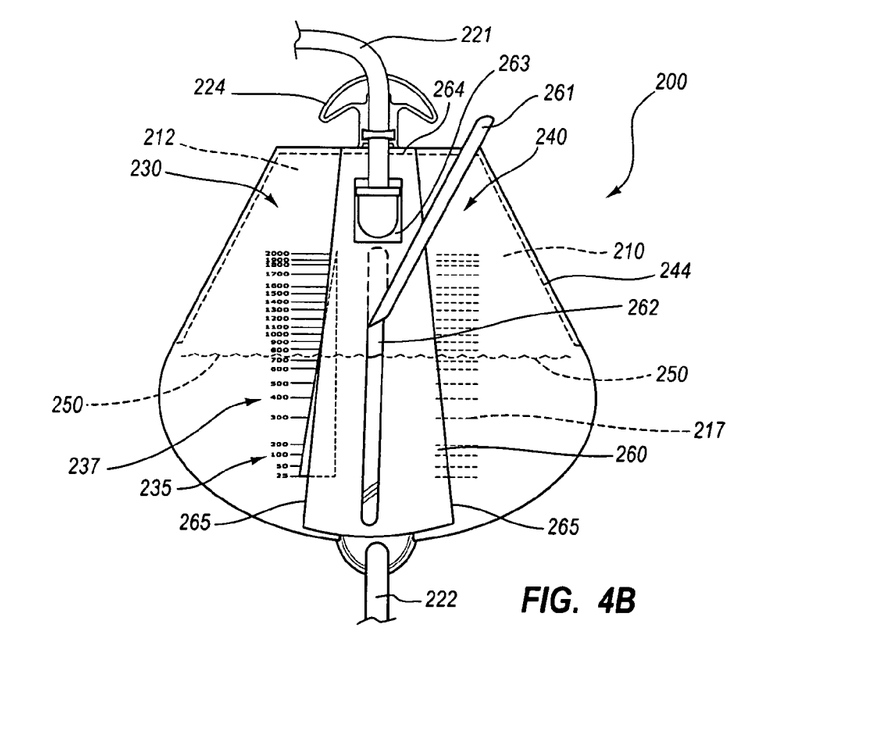
FIG. 4B is a front elevation view of the bodily fluid drainage assembly of FIG. 4A after the assembly has received some fluid.

FIG. 4B depicts bodily fluid bag assembly 200 after the assembly has received some fluid 250. Second volume indicator 235 may be configured to function similarly as second volume indicator 135. As assembly 200 receives fluid 250, fluid bag 210 may expand and cause outer edge 265 and first cover 230 to slide over each other such that fluid level indicator 236 becomes visible. The topmost visible portion of fluid level indicator 236 may correspond with a top level of fluid 250 such that an approximate volume can be determined by correlating the topmost visible portion of fluid level indicator 236 with the nearest graduation 237.

Figure 4C:
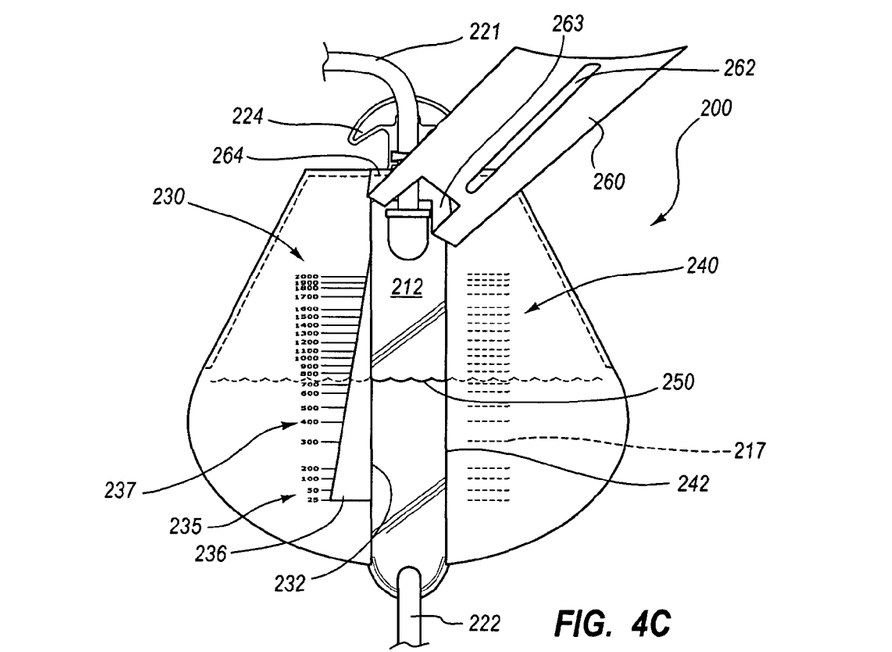
FIG. 4C is a front elevation view of the bodily fluid drainage assembly of FIG. 4B after a portion of the assembly has been torn.

As depicted in FIGS. 4B-4C, third cover 260 may comprise a window cover 261, a cutout 263, and perforations 264. Window cover 261 may comprise a removable opaque plastic that is the same material from which cover 260 is formed. When window cover 261 is removed, a portion of translucent window 262 is revealed such that fluid 250 can be determined.

Window 262 may comprise a portion of translucent front face 212 of fluid bag 210 that is visible between opaque first and second covers 230 and 240.

Figure 4D:
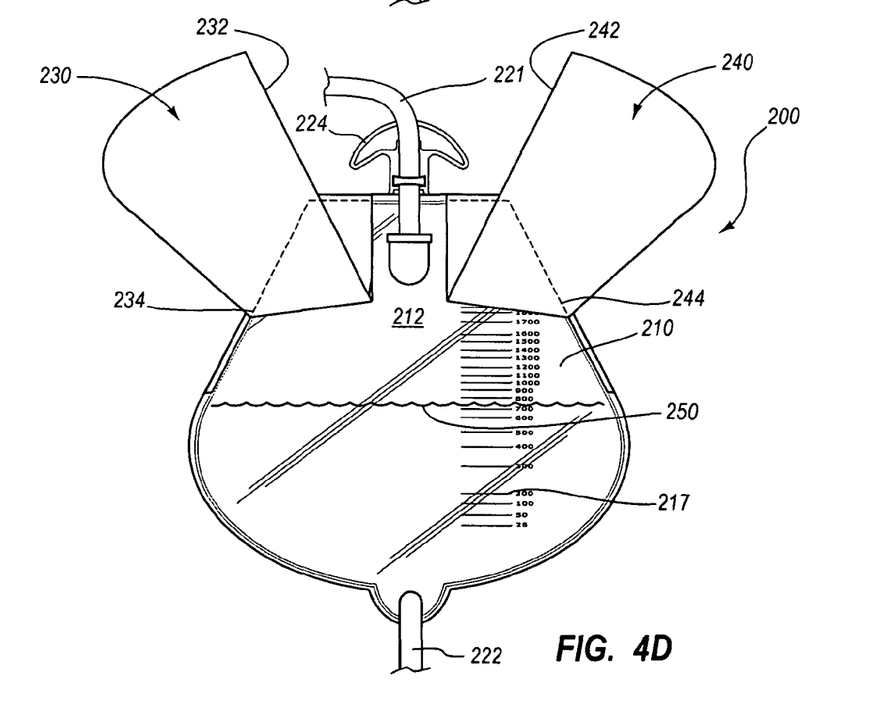
FIG. 4D is a front elevation view of the bodily fluid drainage assembly of FIG. 4C after a portion of the assembly has been removed.

FIG. 4D depicts bodily fluid drainage bag assembly 200 after third cover 260 has been removed and first and second covers have been partially removed. First volume indicator 217 may be used to find an approximate volume of fluid 250 by temporarily lifting or removing second cover 240. First and second covers 230 and 240 may be removed by rupturing perforations 234 and 244 such that front face 212 is entirely revealed and at least the portion of fluid 250 nearest the front face of the fluid bag can be visualized.

Figure 5A:
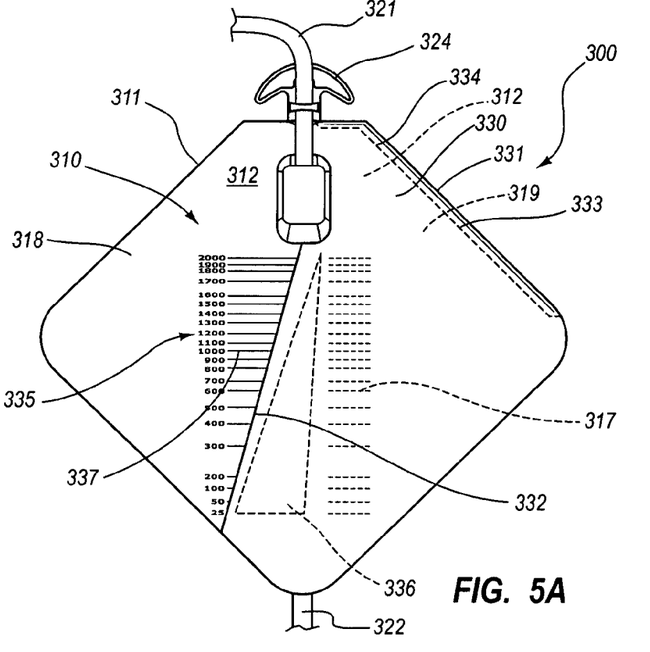
FIG. 5A is a front elevation view of another embodiment of a bodily fluid drainage assembly.
Figure 5B:
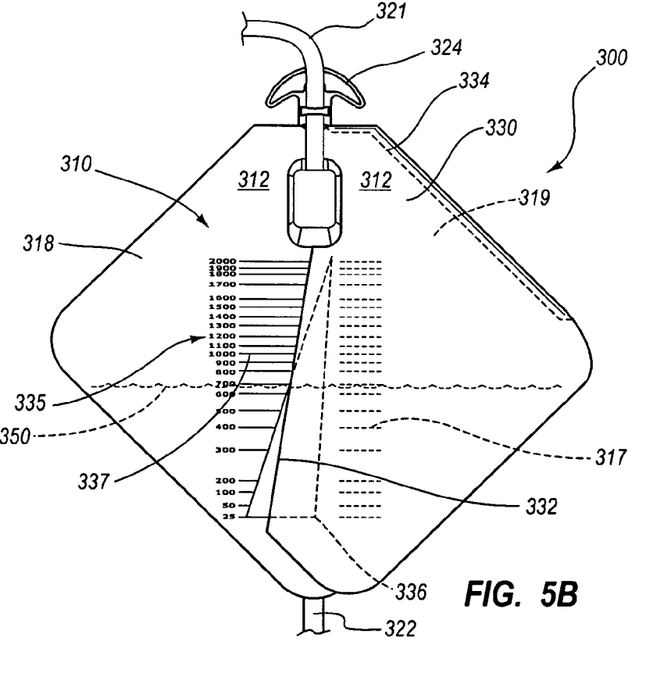
FIG. 5B is a front elevation view of the assembly of FIG. 5A after the assembly has received some fluid.
Figure 5C:
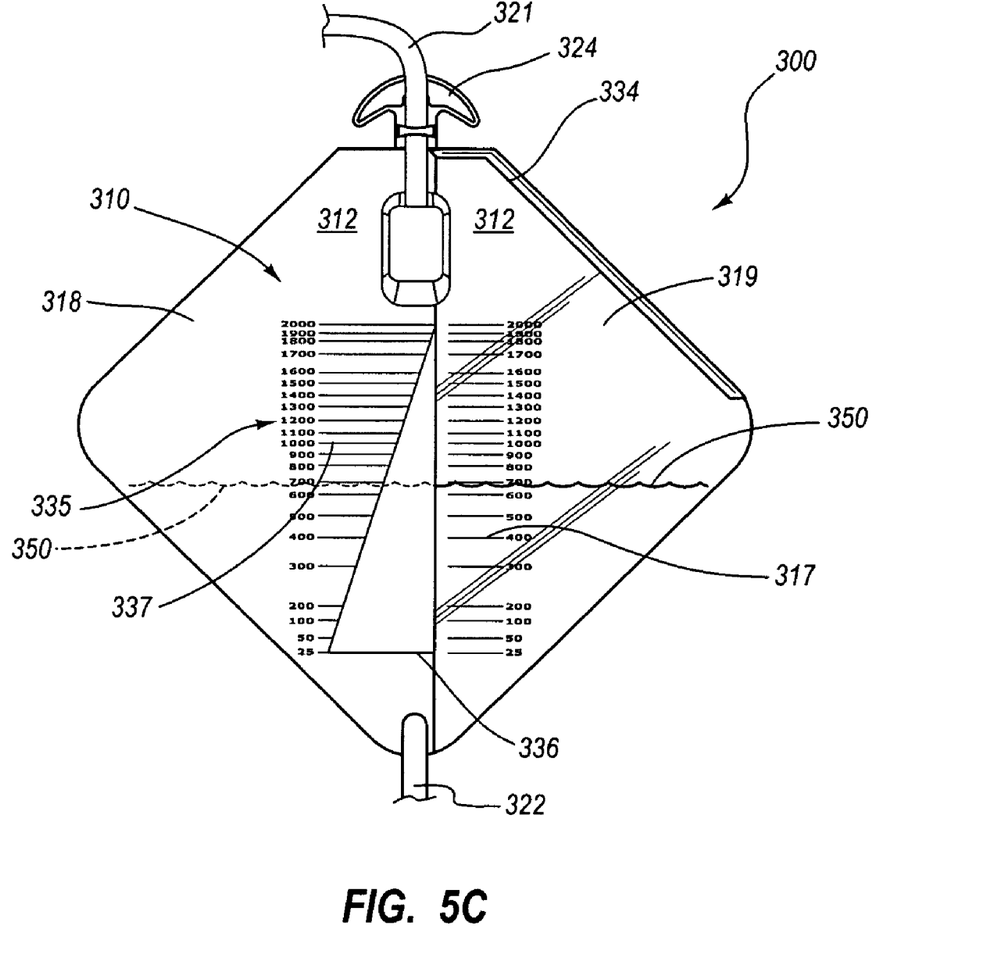
FIG. 5C is a front elevation view of the assembly of FIG. 5B after a portion of the assembly has been removed.

FIGS. 5A-5C depict another embodiment of a bodily fluid drainage bag 300 from front elevation views, wherein FIG. 5A depicts the assembly, FIG. 5B depicts the assembly after the assembly has received some fluid, and FIG. 5C depicts the assembly after a portion of the assembly has been removed. Assembly 300 may be configured similarly and may function similarly as assemblies 100 and/or 200 described herein. Assembly 300 may comprise a fluid bag 310, an inlet tube 321, an outlet tube 322, a hanger 324, and a cover 330.

Fluid bag 310 may comprise an outer edge 311, a front face 312, a first volume indicator 317, a left portion 318, and a right portion 319. Outer edge 311 may comprise a perimeter of fluid bag 310 and may at least partially comprise a seam formed by coupling one or more panels of plastic material together to form the fluid bag. Front face 312 may comprise an opaque left portion 318 and a translucent right portion 319. Left and right portions 318 and 319 are defined strictly for descriptive purposes and the portions themselves and features associated with them may be exchanged or flipped. Left and right portions may or may not define half or approximately half of fluid bag 310 front face 312.

Front face 312 of fluid bag 310 may comprise a translucent plastic material. Right portion 319 is at least partially translucent, except for first volume indicator 317, which may be printed on the right portion. First volume indicator 317 comprises graduations that allow for an approximate volume of a fluid within the bag. An opaque cover 330 is coupled to fluid bag 310 such that the translucent right portion 319 is obscured. Left portion 318 may be rendered opaque by printing, painting, or any other suitable technique and at least a portion of second volume indicator 335 may be printed on the left portion.

Cover 330 may comprise an outer edge 331, an inner edge 332, a seam 333, and perforations 334. Cover 330 comprises an opaque material that is coupled to fluid bag 310 to form seam 333, wherein outer edge 331 is at least partially aligned with a perimeter of the fluid bag. Perforations 334 may be formed in cover 330 such that the cover may be removed from assembly 300 to reveal right portion 319 and first volume indicator 317.

FIG. 5B depicts assembly 300 after the assembly has received a volume of fluid 350. Cover 330 is configured to slide over right portion 318 of bag 310 such that a portion of fluid level indicator 336 is revealed, wherein a topmost revealed portion of the fluid level indicator corresponds to the level of fluid 350. An approximate volume of fluid 350 may be ascertained by locating a graduation 337 that is adjacent to the topmost revealed portion of fluid level indicator 336. As such, an approximate volume of fluid 350 may be determined without directly viewing fluid 350.

FIG. 5C depicts assembly 300 after cover 330 has been removed such that translucent right portion 319 of front face 312 is visible. An approximate volume of fluid 350 can be determined by comparing the top of the fluid to the nearest graduation on first volume indicator 317. Graduations 337 of second volume indicator 335 may or may not report an accurate approximate volume, when compared directly to the top level of fluid 350.

Figure 6:
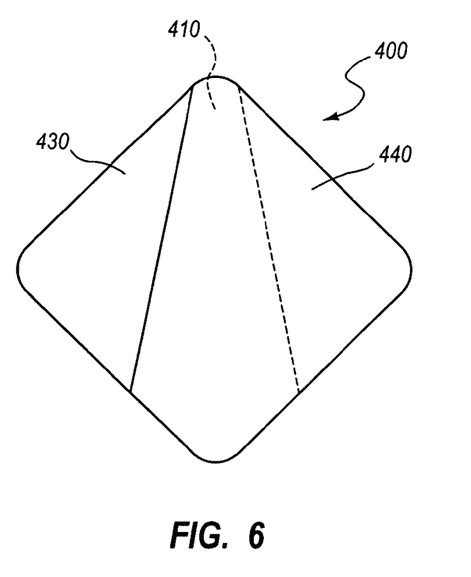
FIG. 6 is a front elevation view of another embodiment of a bodily fluid drainage assembly.
Figure 7:
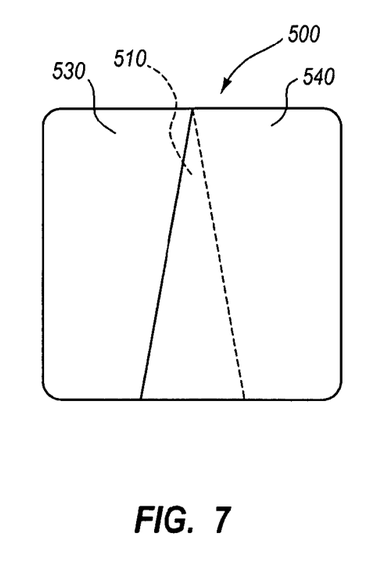
FIG. 7 is a front elevation view of another embodiment of a bodily fluid drainage assembly.
Figure 8:
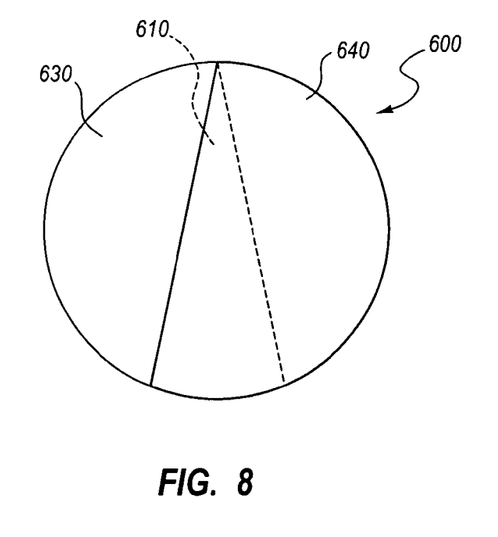
FIG. 8 is a front elevation view of another embodiment of a bodily fluid drainage assembly.
Figure 9:
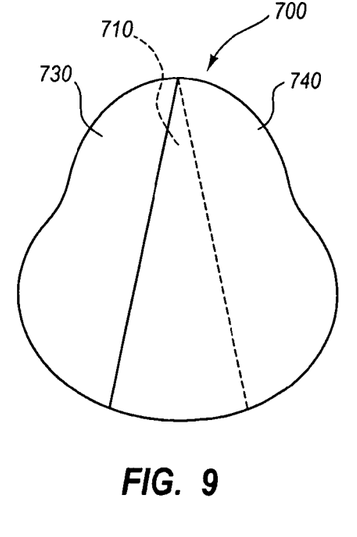
FIG. 9 is a front elevation view of another embodiment of a bodily fluid drainage assembly.

FIGS. 6-8 depict alternative embodiments of bodily fluid drainage assemblies from front elevation views, wherein FIG. 6 depicts assembly 400; FIG. 7 depicts assembly 500; FIG. 8 depicts assembly 600: and FIG. 9 depicts assembly 700. Assemblies 400, 500, 600, and 700 may be configured similarly and may function similarly as assemblies 100, 200, and/or 300 described herein. Assembly 400 may comprise a fluid bag 410, a first cover 430, and a second cover 440. Assembly 400 may further comprise an inlet tube, an outlet tube, and first and second volume indicators as described herein.

Likewise, assembly 500 may comprise a fluid bag 510, a first cover 530, and a second cover 540. Assembly 500 may further comprise an inlet tube, an outlet tube, and first and second volume indicators as described herein. Assembly 600 may comprise a fluid bag 610, a first cover 630, and a second cover 640. Assembly 600 may further comprise an inlet tube, an outlet tube, and first and second volume indicators as described herein. Assembly 700 may comprise a fluid bag 710, a first cover 730, and a second cover 740. Assembly 700 may further comprise an inlet tube, an outlet tube, and first and second volume indicators as described herein.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Without further elaboration, it is believed that one skilled in the art can use the preceding description to utilize the present disclosure to its fullest extent. The examples and embodiments disclosed herein are to be construed as merely illustrative and not a limitation to the scope of the present disclosure in any way. It will be apparent to those having skill in the art that changes may be made to the details of the above-described embodiments without departing from the underlying principles of the disclosure described herein. In other words, various modifications and improvements of the embodiments specifically disclosed in the description above are within the scope of the appended claims. Note that elements recited in means-plus-function format are intended to be construed in accordance with 35 U.S.C. §112 ¶6. The scope of the disclosure is therefore defined by the following claims.

The invention claimed is:

1. A bodily fluid drainage assembly, comprising:
   a fluid bag;
   a first volume indicator;
   a second volume indicator; and,
   at least one cover that at least partially obscures observation of a fluid retained within the fluid bag,
   wherein the assembly is configured such that expansion of the fluid bag in response to receiving the fluid causes at least a portion of the cover to become partially displaced in relation to the second volume indicator such that an approximate volume of the fluid within the fluid bag is indicated at the junction of the cover and the second volume indicator, and wherein the approximate volume of the fluid can be determined without direct observation of the fluid.

2. The bodily fluid drainage assembly of claim 1, wherein at least a portion of the fluid bag is translucent.

3. The bodily fluid drainage assembly of claim 1, wherein the first volume indicator comprises graduations denoted on the fluid bag such that an approximate volume of the fluid can be determined by comparing a top level of the fluid with the graduations.

4. The bodily fluid drainage assembly of claim 1, wherein the at least one cover is removable.

5. The bodily fluid drainage assembly of claim 4, wherein the at least one cover comprises perforations that may be ruptured to remove the cover.

6. The bodily fluid drainage assembly of claim 1, wherein the first volume indicator and the second volume indicator are each located on the fluid bag.

7. The bodily fluid drainage assembly of claim 1, wherein the assembly comprises a first cover and a second cover, and wherein the first volume indicator is located on the fluid bag, the second volume indicator is located on the first cover, and as the fluid bag receives fluid, the second cover becomes displaced in relation to the second volume indicator.

8. The bodily fluid drainage assembly of claim 7, wherein the first and second covers are configured such that at least a portion of each cover is removable from the assembly.

9. The bodily fluid drainage assembly of claim 8, wherein the each of the covers comprise perforations that may be ruptured to remove the covers.

10. The bodily fluid drainage assembly of claim 7, wherein the assembly further comprises a third cover.

11. The bodily fluid drainage assembly of claim 10, wherein the second cover comprises a window cover that defines a portion of the second cover and is configured such that the window cover can be removed without removing the second cover, and wherein removal of the window cover allows fluid within the fluid bag to be visualized.

12. The bodily fluid drainage assembly of claim 10, wherein the third cover is removable from the assembly, and wherein removal of the third cover allows the fluid within the fluid bag to be visualized.

13. The bodily fluid drainage assembly of claim 1, wherein the fluid bag further comprises an inlet tube, an outlet tube, an output regulator and a hanger.

14. A bodily fluid drainage assembly, comprising:
 a fluid bag, comprising:
  a front face, comprising:
   a first volume indicator;
   a second volume indicator;
   an opaque first portion, and
   a translucent second portion;
 a cover coupled to the fluid bag in a predetermined location such that the cover at least partially obscures the translucent second portion, wherein the cover comprises an inner edge, and
 wherein the assembly is configured such that an approximate volume of a fluid retained within the fluid bag is indicated at the junction of the cover and the second volume indicator wherein the approximate volume of the fluid may be determined without direct observation of the fluid.

15. The bodily fluid drainage assembly of claim 14, wherein the first volume indicator comprises graduations located at predetermined positions such that the graduations denote approximate volumes.

16. The bodily fluid drainage assembly of claim 15, wherein the graduations are located on the translucent second portion.

17. The bodily fluid drainage assembly of claim 15, wherein the graduations are located on the opaque first portion such that the graduations are adjacent to the translucent second portion.

18. The bodily fluid drainage assembly of claim 14, wherein the second volume indicator comprises a fluid level indicator and graduations and the cover at least partially obscures the fluid level indicator when the fluid bag has received a volume of fluid that is less than a minimum volume capable of being approximated by the second volume indicator.

19. The bodily fluid drainage assembly of claim 18, wherein receipt of the fluid into the fluid bag that is greater than the minimum volume causes the fluid bag to expand, thereby causing at least a portion of the cover to become partially displaced in relation to the second volume indicator such that the inner edge of the cover slides over the second volume indicator thereby revealing a portion of the fluid level indicator.

20. The bodily fluid drainage assembly of claim 14, wherein the fluid bag further comprises an inlet tube, an outlet tube, a hanger, and an output regulator.

21. A bodily fluid drainage assembly, comprising:
 a fluid bag, comprising:
  a translucent portion, and
  a first volume indicator;
 a first cover, comprising:
  a fluid level indicator, and
  graduations; and;
 a second cover having an inner edge,
 wherein each of the first and second covers are coupled to the fluid bag in predetermined positions such that the second cover obscures the fluid level indicator when less than a predetermined minimum volume of a fluid is retained within the fluid bag, and wherein expansion of the fluid bag upon receiving greater than the predetermined minimum volume of fluid causes the first and second covers to slide across each other such that the inner edge of the second cover reveals a portion of the fluid level indicator thereby allowing an approximate volume to be determined by correlating a point at which the inner edge of the second cover obscures the fluid level indicator and a nearest graduation.

22. The bodily fluid drainage assembly of claim 21, wherein the fluid bag further comprises an inlet tube, an outlet tube, a hanger, and an output regulator.

23. The bodily fluid drainage assembly of claim 21, wherein each of the first and second covers are removable from the assembly by rupturing perforations located on the covers.

24. The bodily fluid drainage assembly of claim 21, wherein the assembly further comprises a third cover.

25. The bodily fluid drainage assembly of claim 24, wherein the second cover comprises a window cover that defines a portion of the second cover and is configured such that the window cover can be removed without removing the second cover, and wherein removal of the window cover allows fluid within the fluid bag to be visualized.

26. The bodily fluid drainage assembly of claim 24, wherein the third cover is removable from the assembly, and wherein removal of the third cover allows the fluid within the fluid bag to be visualized.

27. A means for determining an approximate volume of a fluid retained in a fluid bag without directly observing the fluid, wherein the means for determining an approximate volume comprises: a fluid level indicator, graduations, and; a cover having an inner edge; wherein the cover is coupled to the fluid bag such that the cover at least partially obscures visualization of the fluid within the fluid bag, and wherein the cover also obscures the fluid level indicator when less than a predetermined minimum volume of the fluid is retained within the fluid bag, and wherein expansion of the fluid bag upon receiving greater than the predetermined minimum volume of fluid causes the cover to change position relative to the fluid level indicator, such that the inner edge of the cover reveals a portion of the fluid level indicator thereby allowing an approximate volume to be determined by correlating a point at which the inner edge of the second cover obscures the fluid level indicator and a nearest graduation.

* * * * *